US011871909B2

(12) United States Patent
Kazmi et al.

(10) Patent No.: US 11,871,909 B2
(45) Date of Patent: Jan. 16, 2024

(54) ORTHOTIC DEVICE TO MAINTAIN OR ENLARGE AN ORAL APERTURE

(71) Applicant: The Aga Khan University, Karachi (PK)

(72) Inventors: Syed Murtaza Raza Kazmi, Karachi (PK); Farhan Raza Khan, Karachi (PK)

(73) Assignee: The Aga Khan University, Karachi (PK)

( * ) Notice: Subject to any disclaimer, the term of this patent is extended or adjusted under 35 U.S.C. 154(b) by 761 days.

(21) Appl. No.: 16/990,842

(22) Filed: Aug. 11, 2020

(65) Prior Publication Data

US 2021/0378498 A1     Dec. 9, 2021

(30) Foreign Application Priority Data

Jun. 3, 2020 (PK) .................................... 447/2020

(51) Int. Cl.
*A61B 1/24* (2006.01)

(52) U.S. Cl.
CPC ...................................... *A61B 1/24* (2013.01)

(58) Field of Classification Search
CPC .................................... A61B 1/24; A61B 1/32
See application file for complete search history.

(56) References Cited

U.S. PATENT DOCUMENTS

| 3,735,491 | A | 5/1973 | Pabalan |
| 3,790,712 | A | 2/1974 | Andries |
| 4,071,694 | A | 1/1978 | Pfeiffer |
| 4,220,160 | A | 9/1980 | Kimball et al. |
| 4,254,302 | A | 3/1981 | Walshe |
| 4,589,417 | A | 5/1986 | Eseifan et al. |
| 4,594,731 | A | 6/1986 | Lewkowicz |
| 6,134,331 | A | 10/2000 | Baekgaard |
| 6,219,424 | B1 | 4/2001 | Murphy |
| 7,006,638 | B1 | 2/2006 | Baekgaard et al. |
| 7,115,102 | B2 | 10/2006 | Abbruscato |
| 8,934,637 | B2 | 1/2015 | Habboushe et al. |
| 9,204,856 | B2 | 12/2015 | Bedingham et al. |
| 2009/0270767 | A1 | 10/2009 | Nishihara et al. |
| 2016/0058363 | A1 | 3/2016 | Hayes-Gill et al. |
| 2018/0256057 | A1 | 9/2018 | Khandoker |
| 2018/0353121 | A1 | 12/2018 | Tian et al. |
| 2018/0368753 | A1 | 12/2018 | Yin et al. |

FOREIGN PATENT DOCUMENTS

WO   WO 2013/086112   6/2013

*Primary Examiner* — Tessa M Matthews
(74) *Attorney, Agent, or Firm* — Fish & Richardson P.C.

(57) ABSTRACT

An orthotic device for treating microstomia is described that includes a U-shaped rod, a pair of conformers, and a spring coiled around the rod, positioned between the conformers. The rod includes a curved portion between two straight arms and is sized to accommodate the subject's head. The pair of conformers each include a labial hook and a pair of through holes for receiving the U-shaped rod. The U-shaped rod is smooth through holes of each conformer positioned at the curved portion proximate to a corresponding one of the straight arms. The labial hooks each curve away from the curved portion towards one of the straight arms of the U-shaped rod. During use the labial hooks are inserted in the subject's mouth to engage one of the opposing labial commissures of the mouth. A compression of the spring applies a force to the labial commissures via the conformers.

13 Claims, 3 Drawing Sheets

ORTHOTIC DEVICE TO MAINTAIN OR ENLARGE AN ORAL APERTURE

RELATED APPLICATION

This disclosure claims priority to Pakistan Patent Application No. 447/2020, entitled "Orthotic Device to Maintain or Enlarge an Oral Aperture" and filed on Jun. 3, 2020, the entire contents of which are incorporated herein by reference.

TECHNICAL FIELD

This disclosure relates to an orthotic device, method, and kit for maintaining or enlarging a size of an oral aperture of a patient.

BACKGROUND

Microstomia is a condition defined as a reduction in the size of oral aperture. Such condition may be developmental or acquired. Acquired microstomia may be caused by illness, injury or surgical trauma. This condition may not only cause difficulty in phonetics, mastication, and oral hygiene maintenance but can also lead to psychological dilemmas to the patients. The management of microstomia is multidimensional and multidisciplinary. Dimensions include preventing additional reduction, limiting the harm of the oral aperture reduction, and regaining the oral aperture size. A team of physicians, dentist, speech therapist, occupational therapist, and psychiatrist are often consulted for treatment and recovery.

SUMMARY

In certain aspects, an orthotic device for treating microstomia in a human subject, includes a U-shaped rod (which can be made of stainless steel in some implementations) comprising a curved portion between two straight arms, the U-shaped rod being sized to accommodate the subject's head; a pair of conformers each comprising a labial hook and a pair of through holes for receiving the U-shaped rod, the U-shaped rod being smooth through holes of each conformer and each conformer being positioned at the curved portion proximate to a corresponding one of the straight arms such that the labial hooks each curve away from the curved portion towards a corresponding one of the straight arms of the U-shaped rod; and a spring coiled around the rod and positioned between the conformers; wherein during use the labial hooks are inserted in the subject's mouth to each engage one of the opposing labial commissures of the mouth such that a compression of the spring applies a force to the labial commissures via the conformers.

In some implementations, the conformer comprise a surface shaped to conform to the curved portion of the U-shaped rod.

In some implementations, the conformers are each formed from a single piece of heat cured polymethyl methacrylate (PMMA) material.

In some implementations, the conformers include or are a plastic.

In some implementations, the U-shaped rod can be made of stainless steel, or biocompatible metal or alloy.

In some implementations, the spring is arranged on the U-shaped rod at a center of the curved portion.

In some implementations, the through holes of each conformer are spaced apart by a distance in a range from 1 cm to 5 cm.

In some implementations, the orthotic device also includes a pair of washers, each washer being arranged between a corresponding end of the spring and a corresponding one of the conformers. This prevents the spring from going inside the labial hook. In some implementations, the washers are polytetrafluoroethylene washers.

In some implementations, the orthotic device also includes a pair of retainers attached to the U-shaped rod on respective ends of the straight arms.

In some implementations, the straight arms each include a threaded portion and the retainers are nuts attached to the threaded portions.

In certain aspects, a method of treating microstomia in a human subject, includes administering the orthotic device to apply a force to the subject's labial commissures.

In some implementations, the method further includes adjusting the force applied by replacing the spring with a second spring of differing length and/or stiffness.

The subject matter described herein has many advantages. For example, the orthotic device may provide a treatment plan that is customizable to the patient and can be adjusted as the patient progresses through treatment. The orthotic device may enlarge an oral aperture thereby improving access to dental hygiene maintenance, food consumption, and speech. The components of the device can also be separated for individual sterilization and cleaning of each component. The orthotic device and kit may be easily manufactured and may reduce the cost of production.

The details of one or more implementations of the invention are set forth in the accompanying drawings and the description below. Other features, objects, and advantages of the invention will be apparent from the description and drawings, and from the claims.

BRIEF DESCRIPTION OF THE FIGURES

Like reference symbols in the various drawings indicate like elements.

DETAILED DESCRIPTION

Figure 1:
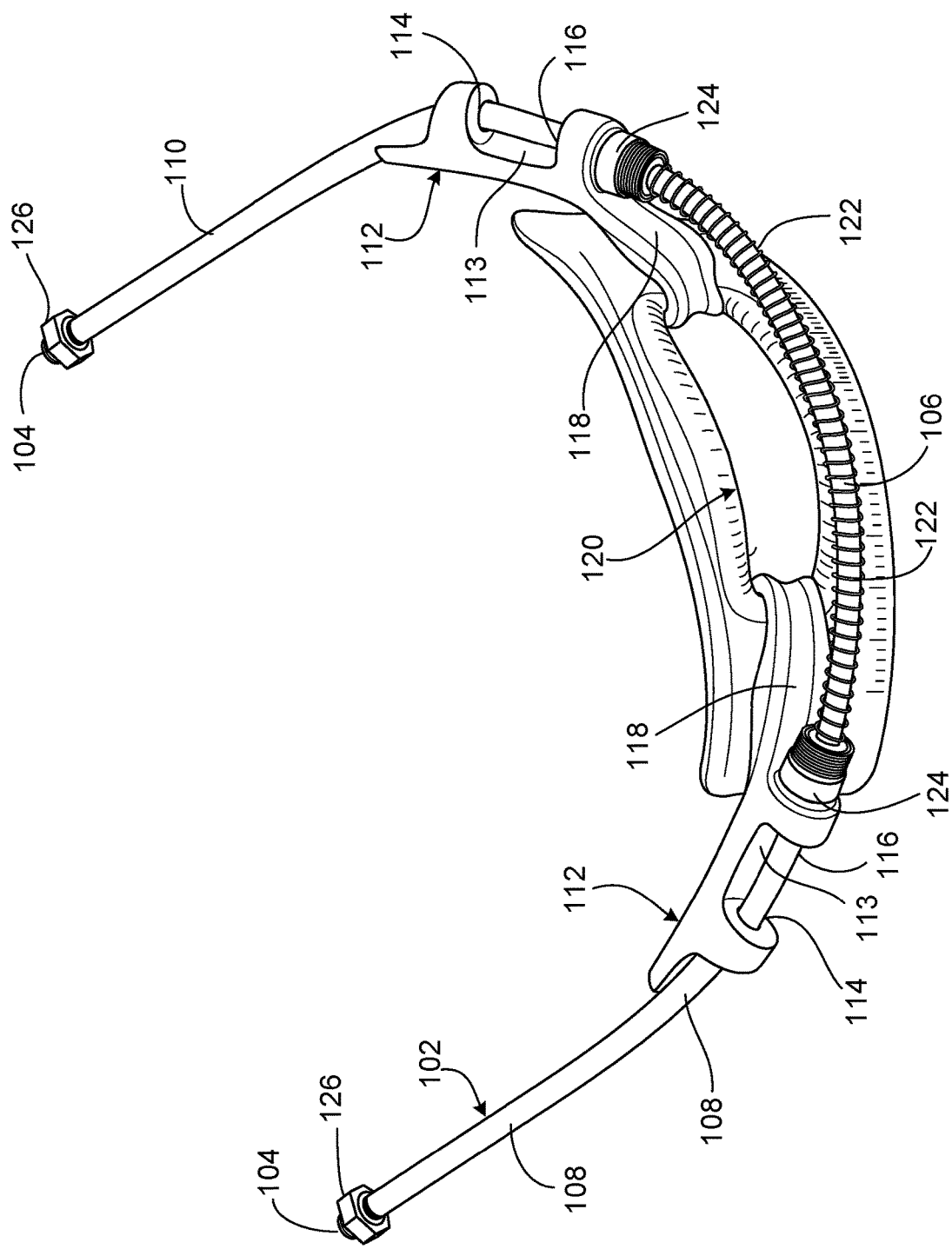
FIG. 1 is a perspective view of an orthotic device engaged with a mouth.
Figure 2:
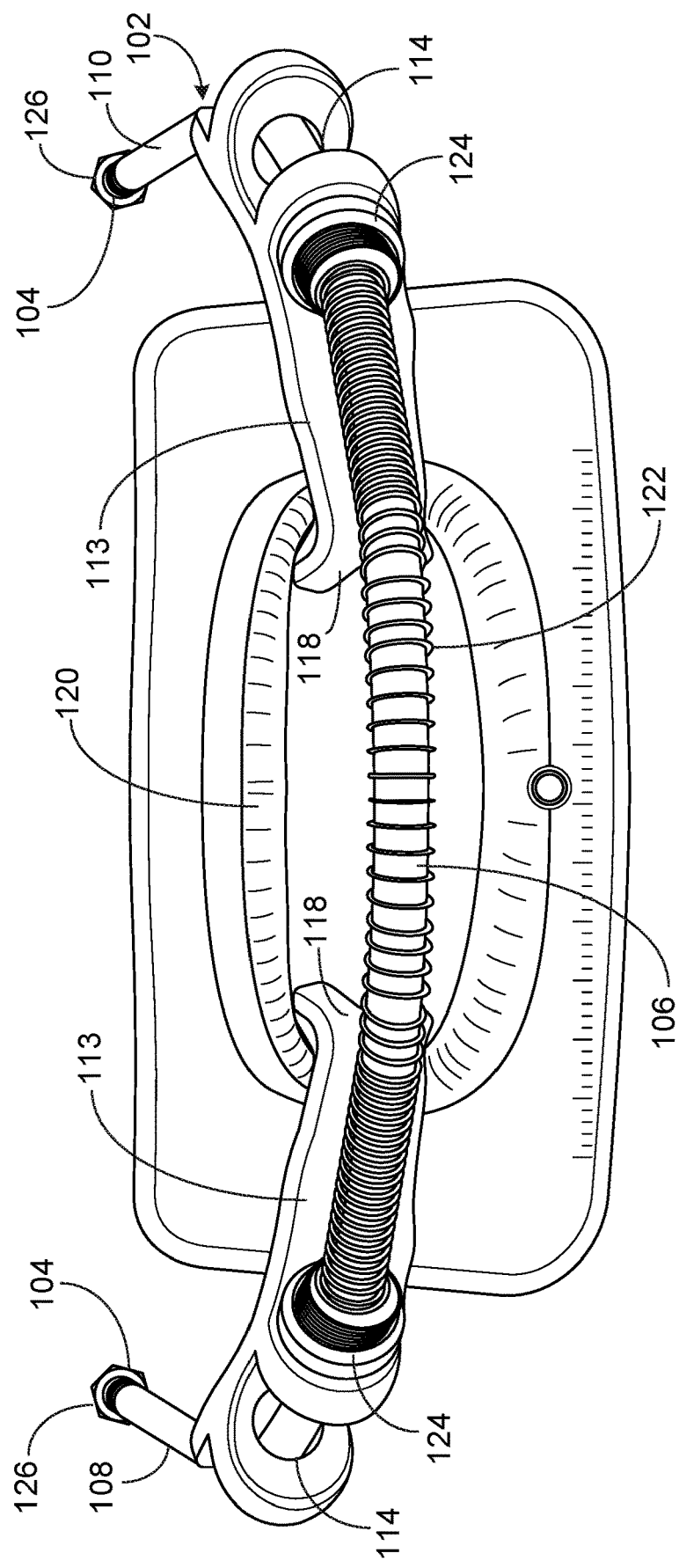
FIG. 2 is a front view of the orthotic device engaged with the mouth.
Figure 3:
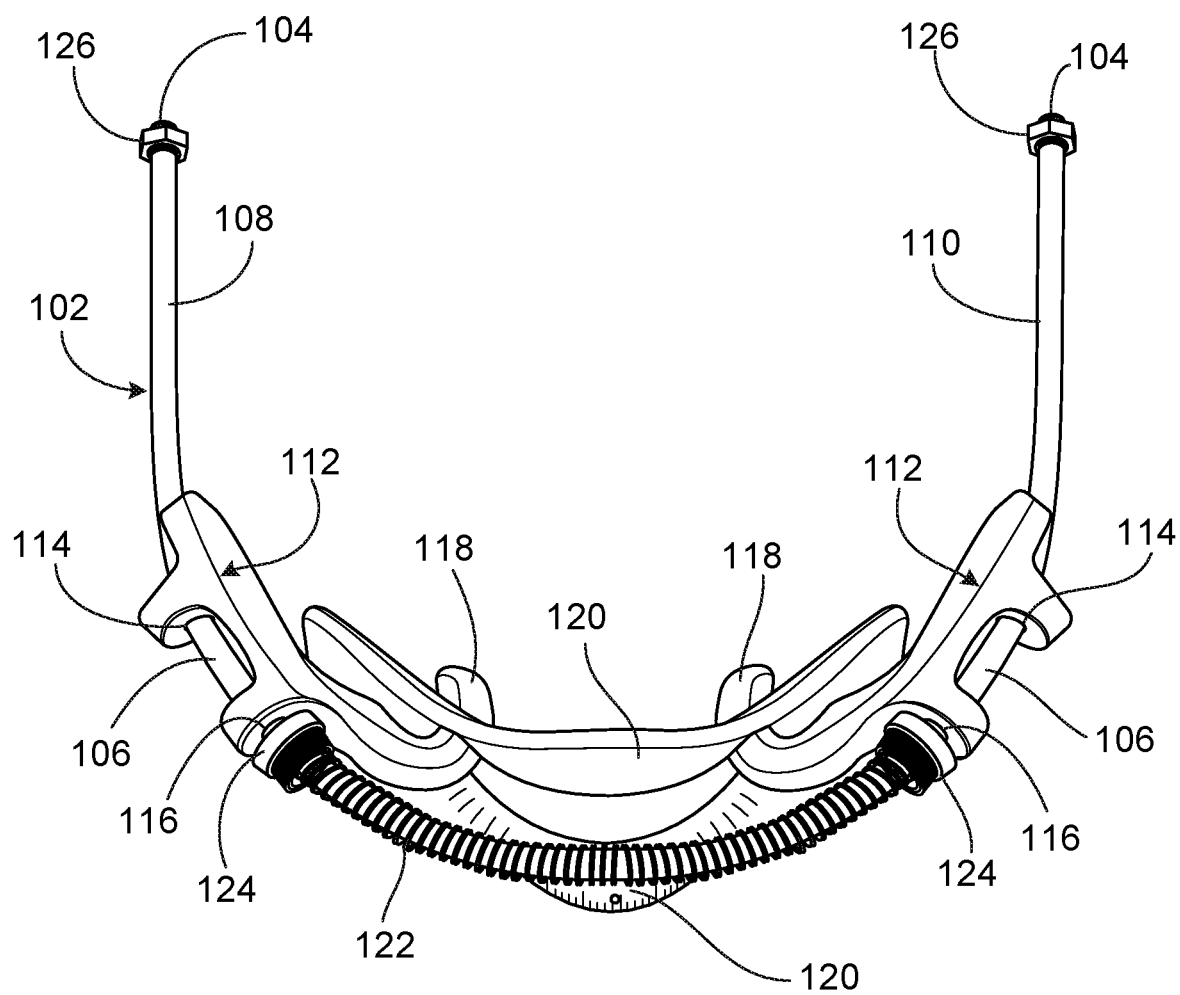
FIG. 3 is a top or bottom view of the orthotic device engaged with the mouth.

FIGS. 1-3 show different views of an orthotic device 100. More particularly, FIG. 1 illustrates a perspective view of the orthotic device 100, FIG. 2 illustrates a front view of the orthotic device 100, and FIG. 3 illustrates a top or bottom view of the orthotic device 100. The orthotic device 100 can be recommended to patients that experience a severe reduction in oral aperture (i.e., mouth) size. The orthotic device 100 is used to enlarge the oral aperture of the patient with little to no discomfort to the patient by applying a constant force on the labial commissures or edges of the mouth. The orthotic device 100 can be available as a kit with a variety of interchangeable components to provide ongoing and customizable treatment outside of a medical facility. The orthotic device 100 can also be referred to as an orthotic, an orthosis, or an orthosis device.

The orthotic device 100 has a body 102 (which can be referred in some implementations as a main metal body).

The body 102 is a "U" shaped rod sized to receive a head of a patient or human subject within the interior of the "U". The body 102 includes a curved (arced) portion 106, a first straight arm 108, and a second straight arm 110. The first straight arm 108 and the second straight arm 110 connect via the curved portion 106 to form the "U" shape. The first straight arm 108 and second straight arm 110 each include a threaded section 104 arranged on the end of the straight arms 108, 110 opposite the curved portion 106. The threaded section 104 engages with compatible threads of a retainer or nut 126. The retainer 126 defines a central aperture that receives the threaded section 104. The retainer 126 is free to rotate relative to the body 102. Rotating the retainer 126 moves the retainer 126 axially along the threaded section 104 due to the threaded engagement. The retainer 126 acts as a lock to prevent other components from disengaging with the body 102. The retainer 126 may also engage with a mount or with ear of the patient (not shown) to help hold the orthotic device 100 static during use. The retainer 126 is removable, for example by rotating the retainer 126 until the retainer 126 disengages with the threaded section 104. When the retainer is removed, components of the orthotic device 100 mounted on the body 102 can be removed from the body 102.

The orthotic device 100 can be narrowed by pressing the first and second arms 108, 110 towards each other or away from each other, narrowing or widening the arc of the curved portion 106 respectively. The distance between the straight arms 108, 110 is generally the width of an average sized head, about 35.5 centimeters to about 40.5 centimeters (cm). The distance can be lengthened or shortened between a range of 20 cm to 55 cm. The U-shaped body 102 is made of stainless steel, or any biocompatible metal or alloy. Some bodies are made of a plastic or combination of metal, alloy, and/or plastic.

The orthotic device 100 also includes conformers 112 movably mounted on the body 102. The conformers 112 have a surface 113 on which a first hole 114 and a second hole 116 are defined. The surface 113 is curved to conform to the curved portion 106 of the U-shaped body 102. The first hole 114 and second hole 116 are sized to receive the body 102. The first hole 114 and the second hole 116 are spaced about 1 cm to about 5 cm apart on the conformer. The curved portion 106 is smooth and has compression spring 122 between both the conformers 112 so that the conformers 112 are pushed against each other and free to translate along the body 102. Each conformer 112 also includes a labial hook 118 that engages with the corner of mouth 120 of a patient. Each conformer 112 is positioned at the curved portion 106 proximate to a corresponding one of the straight arms 108, 110 such that the labial hooks 118 each curve away from the curved portion 106 towards a corresponding one of the straight arms 108, 110 of the U-shaped body 102. The labial hooks 118 engage the mouth 120 by hooking onto the edge of the corner of mouth 120 from the outside of the mouth 120, as shown in FIGS. 1-3. The conformers 112 are each formed from a single piece of material, for example a plastic or polymethyl methacrylate (PMMA). In some implementations the conformers are made from multiple types of material. The conformers are translatable along the curved portion 106 and along the straight arms 108, 110. If the retainers 126 are removed the conformers 112 can slide along the straight arms 108, 110 to disengage the conformers 112 and the body 102.

The orthotic device 100 also includes at least one resilient component arranged to apply a force to the conformers 112. In the orthotic device 100, the resilient component is a spring 122 arranged between the conformers 112 on the curved portion 106 of the body 102. The spring 122 is compressed and applies an expanding or compressive force to the conformers 112. Washers 124 are arranged between the spring 122 and the conformers 112 to uniformly transfer the force from the spring 122 to the conformers 112. The washers 124 attach to each end of the spring 122 and are made of or comprise polytetrafluoroethylene (Teflon). In the orthotic device 100, the spring 122 is centered on the curved portion 106 of the body, however, in other devices, the spring may be arranged off center. The resilient components is removable from the body 102, the spring 122 may be translated from the curved portion 106 towards the threaded section 104 of the straight arms 108, 110. If the retainer 126 is removed, the spring 122 may translate to disengage with the body 102.

The orthotic device 100 may be recommended to patients with microstomia. Microstomia is a condition defined as reduction in the size of oral aperture due to illness, injury, or surgical trauma. The orthotic device 100 can be applied to the oral aperture 120 to enlarge the oral aperture. Use of the orthotic device is described with reference to the orthotic device 100, but may be used with any other orthotic device. In use, device receives the patient's head to size the orthotic device 100. The straight arms 108, 110 should tuck behind the ears, similar to wearing glasses. If the straight arms 108, 110 are too far apart, the user presses the straight arms 108, 110 together to narrow the arc of the curved portion 106. If the straight arms 108, 110 are too close together, the user presses the straight arms 108, 110 away from each other to widen the arc of the curved portion 106. Once the proper width is found, the orthotic device 100 receives the head of the patient and the straight arms 108, 110 tuck into the ears of the patient. At this point, the spring 122 is centered in curved portion 106 and is unbiased such that the spring 122 does not apply a force onto the conformers 112. The user then presses the conformers 112 together, compressing the spring 122, and engages the hooks 118 with the labial commissures of the oral aperture (mouth). The spring 122 may expand slightly to engage the hooks 118 with the labial commissures but does not expand to its unbiased configuration. The compressed spring 122 applies an outward force onto the washers 124 which applies the outward force to the conformers 112. The conformers 112 then apply the outward force to the labial commissures of the mouth 120, over time enlarging the mouth. After repeated use, the mouth enlarges.

At this point, the user may replace the spring 122 with a new spring that is longer and/or stiffer than the previous spring. This may be determined by measuring the size of the enlarged mouth and determining that a new spring is appropriate. A longer and/or stiffer spring applies a larger outward force to the labial commissures, thereby enlarging the mouth further. The longer/stiffer spring may have initially been excessively uncomfortable before the mouth was slightly enlarged. To replace the spring 122. The user removes one or both of the retainers 126 by rotating the retainer until the retainer 126 is no longer engaged with the threaded section 104. Once the retainer 126 is removed the user then slides one or both of the conformers 112 from the curved portion 106 towards the threaded section 104 of the straight arms 108, 110 to remove the conformer(s) 112. The user then moves the spring 122 from the curved portion 106 towards the threaded section 104 of one of the straight arms 108, 110 to remove the spring 122. A new spring may then be mounted onto the body 102. The new spring, and washer attached to the spring, receives the straight arm 108 and slides towards the curved portion 106 until the spring is centered on the curved portion. The conformer 112 receives the body 102 (hook end first) and slides from the threaded section 104 towards the curved portion 106 until the conformer 112 abuts the washer of the new spring. The retainer 126 is then reattached and the orthotic device is ready for use.

The conformers 112 may also be replaced by a variety of different conformers. Different conformers include conformers with wide hooks, narrow hooks, thicker hooks, thin hooks, or different materials, such as soft plastics or hard plastics. The terms "wide hook" and "narrow hook" relate to the tightness of the hook's curve. The terms "thick hook" and "thin hook" refer to the amount of material of the hook that touches the labial commissures. The hook narrowness of the conformer may be increased or decreased to improve comfort. The hook thickness of the conformer may be increased or decreases to improve comfort. In some implementations, different types of conformers can be mounted on the first arm 108 and the second arm 110 respectively. This may occur when one side of the mouth has enlarged more than the other, or when one side is more deformed than the other.

The orthotic device 100 may be a part of an orthotic kit (not shown) that includes a variety of mountable springs and a variety of mountable conformers. The springs and conformers allow a customizable treatment plan that can be tailored to the patient based on severity of the deformation, comfort level of the patient, time commitment available, and progression of the treatment.

The orthotic device may also be referred to as a commissure splint, a microstomia prevention appliance, a labial commissure, or a mouth conformer.

While U-shaped bodies have been described, some orthotic devices can have the shape of a circle, a rectangle, a polygon, or any other shape configured to receive the head of a patient.

The orthotic device 100 has been previously discussed as mounted on the patient by tucking the straight arms 108, 110 into the ears of the patient, however, in some implementations, the orthotic device includes ear hooks that encircle the ear, similar to glasses or bifocals. In some implementations, the straight arms connect to a latching device that can be latched (i.e., tied, velcroed, snapped) around the patient's head. In some implementations, engagement of the hooks of the conformers both enlarges the mouth and mounts the orthotic device onto the patient.

While the at least one resilient component has been described as a single spring 122 mounted on the body 102 between the conformers 112, other resilient components are also possible, for example, a compressed piece or resilient material arranged between the conformers. The at least one resilient component may be a pair of magnets each arranged on a hooks 118 of the conformer. The magnets are arranged to repel each other and press the conformers away from each other. The kit may include a variety of magnets with varying strengths.

In some alternate implementations, the at least one resilient component is a first spring and a second spring arranged on the first straight arm and the second straight arm. The first and second springs attach to the retainer or attach to washers that attach to the container. The first and second springs also attach to the conformers or attached to washers that are attached to the conformer. The first and second springs are pulled towards the curved portion into an extended position to engage the hooks of the conformers with the labial commissures and apply an outward force on the labial commissures to enlarge the mouth.

While the retainer 126 has been described as a nut in threaded engagement with the threaded section 104, the retainer may also be a hook around the ears. In other implementations, the retainer may be magnetically engaged with the straight arms, frictionally engaged with the straight arms, or engages with a groove on the straight arms to hold the retainer in place. Some retainers may be made of or comprise an elastic plastic.

Many implementations of the invention have been described. Nevertheless, it will be understood that various modifications may be made without departing from the spirit and scope of the invention. Accordingly, other implementations are within the scope of the claims below. The term patient, as used herein, refers to a human being. In other implementations, the patient can be an animal. Further, in some implementations, the patient can also refer to any user or wearer of the orthotic device 102. Other implementations are within the scope of the following claims.

What is claimed is:

1. An orthotic device for treating microstomia, the orthotic device comprising:
   a U-shaped rod comprising a curved portion between two straight arms, the U-shaped rod being sized to accommodate the subject's head;
   a pair of conformers each comprising a labial hook and a pair of through holes for receiving the U-shaped rod, each conformer being positioned at the curved portion proximate to a corresponding one of the straight arms such that the labial hooks each curve away from the curved portion towards a corresponding one of the straight arms of the U-shaped rod; and
   a spring coiled around the rod and positioned between the conformers;
   wherein during use the labial hooks are inserted in the subject's mouth to each engage one of the opposing labial commissures of the mouth such that a compression of the spring applies a force to the labial commissures via the conformers.

2. The orthotic device of claim 1, wherein the conformer comprise a surface shaped to conform to the curved portion of the U-shaped rod.

3. The orthotic device of claim 1, wherein the conformers are each formed from a single piece of material.

4. The orthotic device of claim 1, wherein the conformers comprise a plastic.

5. The orthotic device of claim 1, wherein the U-shaped rod is made of stainless steel, or biocompatible metal or alloy.

6. The orthotic device of claim 1, wherein the spring is arranged at a center of the curved portion.

7. The orthotic device of claim 1, wherein the through holes of each conformer are spaced apart by a distance in a range from 1 cm to 5 cm.

8. The orthotic device of claim 1, further comprising a pair of washers, each washer being arranged between a corresponding end of the spring and a corresponding one of the conformers.

9. The orthotic device of claim 8, wherein the washers are polytetrafluoroethylene washers.

10. The orthotic device of claim 1, further comprising a pair of retainers attached to the U-shaped rod on respective ends of the straight arms.

11. The orthotic device of claim 10, wherein the straight arms each comprises a threaded portion and the retainers are nuts attached to the threaded portions.

12. A method of treating microstomia, comprising administering the orthotic device of claim 1 to apply a force to the subject's labial commissures.

13. The method of claim 12, further comprising adjusting the force applied by replacing the spring with a second spring of differing length and/or stiffness.

\* \* \* \* \*